United States Patent [19]

Devaney, Jr. et al.

[11] Patent Number: 4,746,614
[45] Date of Patent: May 24, 1988

[54] EXTRACTION DEVICE

[75] Inventors: Mark J. Devaney, Jr., Rochester; Thomas W. Glanville, Churchville, both of N.Y.

[73] Assignee: Eastman Kodak Company, Rochester, N.Y.

[21] Appl. No.: 98,247

[22] Filed: Sep. 18, 1987

[51] Int. Cl.$^4$ ............................................. C12M 1/30
[52] U.S. Cl. ................................... 435/295; 206/564
[58] Field of Search ............... 435/294, 295; 206/569, 206/564

[56] References Cited

U.S. PATENT DOCUMENTS

| 3,116,828 | 1/1964 | Glassman | 206/564 |
| 4,014,746 | 3/1977 | Greenspan. | |
| 4,014,748 | 3/1977 | Spinner et al.. | |
| 4,153,160 | 5/1979 | Leigh | 206/564 |
| 4,618,576 | 10/1986 | Rosenstein et al.. | |

Primary Examiner—Carroll B. Dority, Jr.
Attorney, Agent, or Firm—Dana M. Schmidt

[57] ABSTRACT

There is described a device used with a swab to extract biological material collected on the absorbent end of the swab. The device comprises a container having an internal surface defining a major cavity for confining an extracting liquid medium, and means in said container defining a notch extending into a portion of said internal surface, said notch being configured to receive a swab-like collector and to hold such a collector in said major cavity, said notch having one end that is deeper within said cavity than the rest of said notch, said end being configured to hold the absorbent end of such a collector, and centering means in said container for centering a pipette for aspiration of such extracting medium, said centering means being disposed generally about a line that intersects said notch at a point generally adjacent said one end.

8 Claims, 3 Drawing Sheets

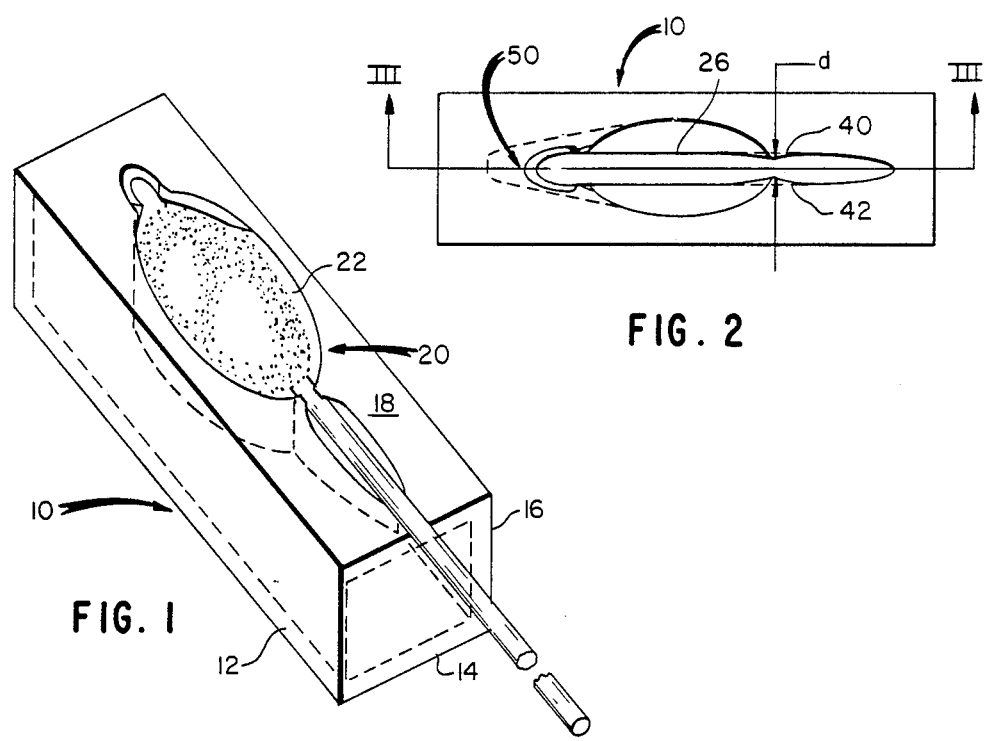
FIG. 2
FIG. 1
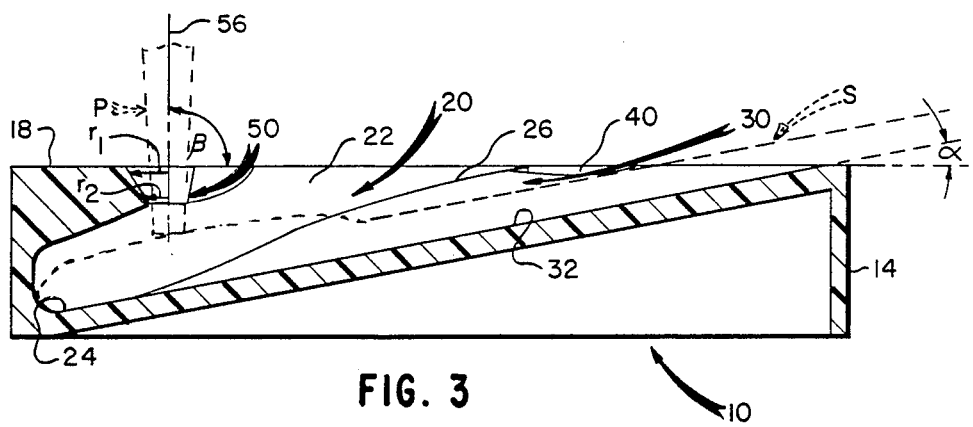
FIG. 3

EXTRACTION DEVICE

FIELD OF THE INVENTION

This invention relates to a device used for extracting biological material from a swab, for example, cells from a throat specimen.

BACKGROUND OF THE INVENTION

It is common practice to obtain a biological specimen from a patient via a swab, and then to extract the particular biological material of choice from the swab. The extraction step uses a liquid particularly adapted for the extraction, based upon the choice of solvent and the optional addition of enzymes. Frequently the extraction takes place in a test tube, followed by a suitable transfer of the extracting liquid to a sample plate for analysis. Examples of such a procedure appear in U.S. Pat. No. 4,618,576.

The procedure described has been less than completely satisfactory because the test tubes used have not been conducive to the use of a minimum of extracting fluid. As a result, the biological material of choice has been substantially diluted. This results from the generally large volume of the test tube and the construction of such a container for delivery of the resultant extracted material by pouring off. In addition, little is provided in the test tube to encourage total extraction of the biological material, or the fluid, from the swab.

There has been a need, therefore, prior to this invention, for an improved container to be used with a swab in the extracting step.

SUMMARY OF THE INVENTION

We have constructed a container for such extraction step that solves the aforesaid problems concerning the use of test tubes.

More specifically, there is provided a device for extracting biological materials from a swab-like collector using a pipette. This device comprises a container having an internal surface defining a major cavity for confining an extracting liquid medium, and means in the container defining a notch extending into a portion of the internal surface, the notch being configured to receive a swab-like collector and to hold such a collector in the major cavity, the notch having one end that is deeper within the cavity than the rest of the notch, the end being configured to hold the absorbent end of such a collector, and centering means in the container for centering a pipette for aspiration of such extracting medium, the centering means being disposed generally about a line that intersects the notch at a point generally adjacent the one end, whereby the maximum amount of extracting medium and biological material is aspiratable out of the major cavity and such a collector, respectively, by a pipette positioned on the line.

Thus, it is an advantageous feature of the invention that an extraction device is provided that extracts the maximum amount of biological material from a swab using a limited amount of extracting medium.

It is a related advantageous feature of the invention that such a device is provided which allows the effective use of a pipette to remove the extracted biological material.

Other advantageous features will become apparent upon reference to the following Description of the Preferred Embodiments, when read in light of the attached drawings.

BRIEF DESCRIPTION OF THE DRAWINGS

FIG. 1 is an isometric view partially broken away, of a device constructed in accordance with the invention, showing a swab in place in the device;

FIG. 2 is a plan view of the device by itself;

FIG. 3 is a section view taken generally along the line III—III of FIG. 2, and showing portions of the swab and a pipette in phantom;

DESCRIPTION OF THE PREFERRED EMBODIMENTS

Figure 4:
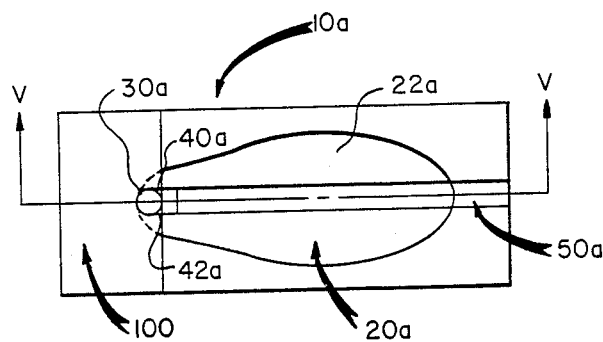
FIG. 4 is a plan view similar to that of FIG. 2, but illustrating an alternate embodiment.

The device of the invention is described in connection with the preferred embodiments, wherein a swab is used as the collecting means for collecting specimen from a patient, and extracted material is aspirated by a pipette. In addition, the device of the invention is useful with other similar collectors, such as a dip stick having absorbent pads at one end thereof. It is also useful with aspirators besides pipettes. Thus, the invention is to the extracting device, rather than to any particular form of collecting means used to place the specimen into the device for extraction, or to a particular aspirator used to remove the liquid used in the extraction.

Terms such as "top", "vertical", "above" and the like refer to portions of the device as it is oriented in its position of use.

Thus, referring to FIGS. 1–3, an extraction device constructed in accord with the invention comprises a container 10 having supporting legs 12, 14 and 16, FIG. 1. The container has a top surface 18. A major cavity 20 is molded into the container, as formed by internal surface 22. Cavity 20 provides the confinement of the extracting liquid medium, and is shaped with a deep end 24, FIG. 3, that is generally at an end of container 10 opposite to the leg 14 and provides an additional leg of support. The bottom extent of cavity 20 is indicated by edge 26, FIG. 3. Top surface 18 limits the extent of cavity 20 and its contents. Thus, cavity 20 slopes downwardly, generally right to left, as measured at its bottom surface 26. The volume of cavity 20 is variable, depending on how large is container 10. Most preferably, however, that volume is kept small to reduce the dilution effect. A useful example of such volume of cavity 20 by itself, is about 0.8 ml.

To hold a swab (S, shown in phantom, FIG. 3) in proper position within cavity 20, internal surface 22 is provided with a notch 30, which extends below the bottom 26 of cavity 20. Notch 30 has a bottom surface 32 that is inclined at an angle alpha with respect to top surface 18. Angle alpha can vary generally from about 2° to about 60°, and most preferably is about 16°.

Notch 30 and bottom surface 32 thereof are an extension of cavity 20, since both are formed by the same molded, internal surface 22. Thus, notch 30 contributes to the volume of cavity 20, for example, about 0.2 ml. Thus the total volume of cavity 20 and notch 30 is about 1.0 ml.

To temporarily retain the swab in position in notch 30, surface 22 is optionally provided with protruding lips 40, 42 adjacent top surface 18, on each side of the notch. The distance d, FIG. 2, between lips 40, 42 is such that a swab can be snapped into notch 30, and then forcibly pulled therefrom. For example, "d" can be about 1.5 mm.

To properly center a pipette P, shown in phantom, FIG. 3, centering surface 50 is provided in internal surface 22, adjacent deep end 24. Such centering surface is shaped with an internal radius $r_1$ at top surface 18 that is larger than the internal radius $r_2$ located further into cavity 20. The orientation of surface 50 is generally vertical, that is, about an axis 56 that extends at an angle beta to top surface 18. Most preferably, beta is generally about 90°. Axis 56 is also the centering line for insertion of pipette P into the device to aspirate up the liquid medium used for extraction.

Therefore, surface 50 is shaped to generally center and support the pipette P for aspiration of the extracting liquid.

The use of the device will be readily apparent from the preceding description. That is, a swab is disposed within notch 30 with the absorbent end at deep end 24 of cavity 20. An appropriate extracting medium is poured into cavity 20, and allowed to act on the swab. Such liquids are conventional and need no further description. Optionally, swab S is reciprocated and rotated along notch 30, towards and away from deep end 24, as a means for agitating the extracting liquid and to encourage the extraction of the biological material. After an appropriate length of time, for example, 1 to 10 min., a pipette P of any suitable construction is inserted along axis 56 down on top of the absorbent end of the swab (shown in phantom, FIG. 3). In this position, most of the extracting medium can be sucked into the pipette. Furthermore, because the pipette is aligned with the absorbent end of the swab, the suction action by the pipette acts to pull off any biological material tending to remain behind on the absorbent material.

The angle between the positioning of swab S and the positioning of pipette P an axis 56 is (beta-alpha).

Figure 6:
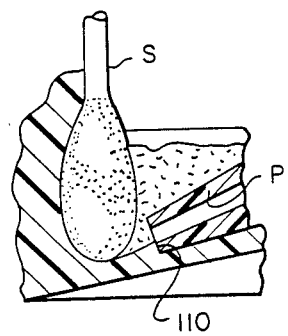
FIG. 6 is an enlarged, fragmentary, section view taken of a portion of the device of FIG. 5, on the same section line, illustrating in greater detail the use of the device of FIG. 4.
Figure 5:
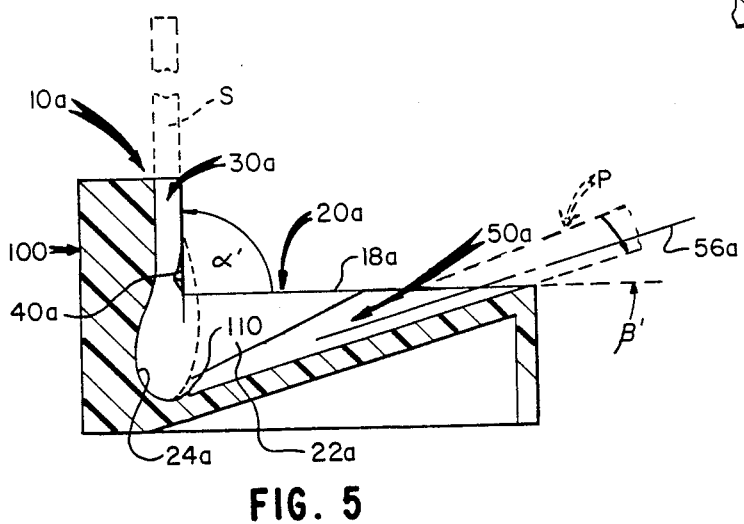
FIG. 5 is a section view taken along line V—V of FIG. 4.

It is not necessary, however, that the angle (beta-alpha) be achieved only by orienting the pipette vertically. That is, the positions of the swab S and pipette P can be reversed, as shown in FIGS. 4–6. Parts similar to those previously described bear the same reference numeral, to which the distinguishing suffix "a" has been appended. Thus, container 10a has a cavity 20a generally constructed as in the previous embodiment, with an internal surface 22a and a deep end 24a, FIG. 5. However, notch 30a for swab S, instead of extending below cavity 20a, is provided in a portion 100 rising vertically above the limiting surface 18a that defines the top of cavity 20a. Thus, notch 30a extends at an angle alpha' to surface 18a that is generally 90°. Notch 30a is also preferably enlarged at deep end 24a, to accommodate the absorbent end of the swab. Lips 40a and 42a are provided as in the previous embodiment.

To center pipette P, shown in phantom, surface 22a is provided with a centering surface 50a that extends below the bottom extreme edge 26a of cavity 20a, FIG. 5. That surface provides a centering axis 56a that is inclined to surface 18a at an angle beta', which has a value between about 2° and 60°, and preferably about 16°. Centering surface 50a preferably terminates at a stop 110 that locates the aperture of pipette P adjacent swab S, FIG. 6.

Figure 7:
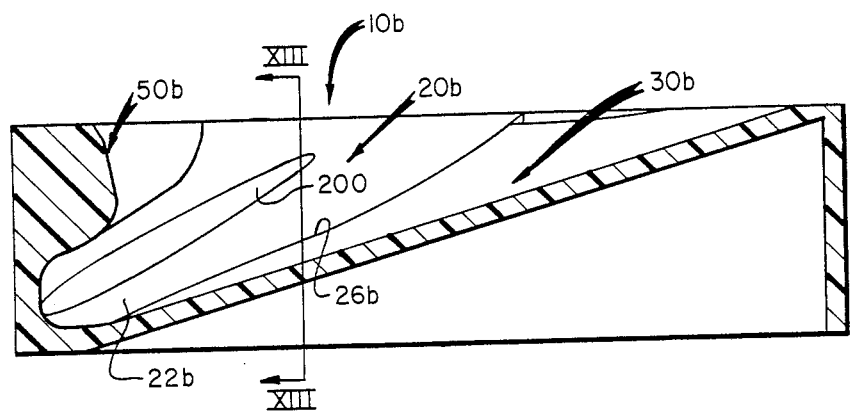
FIG. 7 is a section view similar to that of FIG. 3, except it illustrates yet another embodiment.
Figure 8:
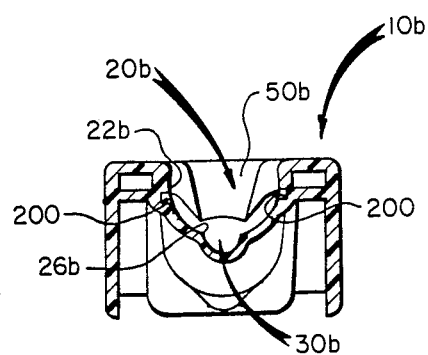
FIG. 8 is a section view taken generally along the line VIII—VIII of FIG. 7.

Antisplash features are optionally included in internal surface 22, as shown in FIGS. 7 and 8. Parts similar to those previously described bear the same reference numeral to which the distinguishing suffix "b" is added. Thus, container 10b has a cavity 20b, notch 30b, and centering surface 50b, all substantially identical to that described in the embodiment of FIGS. 1–3. In addition, however, internal surface 22b has been folded outwardly at 200 to provide two grooves, each on opposite sides of notch 30. These grooves act to damp out any splashing that might occur when swab S is pushed back and forth along notch 30b. Most preferably they extend generally parallel to bottom edge 26b of cavity 20b.

Useful materials for the device of the invention include molded plastic, for example, polyethylene, polypropylene and the like.

The invention has been described in detail with particular reference to preferred embodiments thereof, but it will be understood that variations and modifications can be effected within the spirit and scope of the invention.

What is claimed is:

1. A device for extracting biological materials from a swab-like collector using a pipette, the device comprising:
   a container having an internal surface defining a major cavity for confining an extracting liquid medium, and
   means in said container defining a notch extending into a portion of said internal surface, said notch being configured to receive a swab-like collector and to hold such a collector in said major cavity, said notch having one end that is deeper within said cavity than the rest of said notch, said end being configured to hold the absorbent end of such a collector,
   and centering means in said container for centering a pipette for aspiration of such extracting medium, said centering means being disposed generally about a line that intersects said notch at a point generally adjacent said one end,
   whereby the maximum amount of extracting medium and biological material is aspiratable out of said major cavity and such a collector, respectively, by a pipette positioned on said line.

2. A device as defined in claim 1, wherein said major cavity has a top limiting surface and said notch extends at an angle to said limiting surface that is between about 2° and about 60°.

3. A device as defined in claim 2, wherein said pipette-centering line extends generally perpendicular to said limiting surface.

4. A device as defined in claim 1, wherein said major cavity has a top limiting surface and said notch extends generally perpendicular to said limiting surface.

5. A device as defined in claim 4, wherein said pipette-centering line extends at an angle to said limiting surface that is between about 2° and about 60°.

6. A device as defined in claim 1, wherein said container further includes means in said notch for retaining a swab-like collector temporarily within the notch.

7. A device as defined in claim 1, wherein the volumes of said major cavity and said notch together do not exceed about 1.0 ml.

8. A device as defined in claim 1, and further including means in said container for damping splashing when a swab is reciprocated in said notch.

* * * * *